(12) United States Patent
Li et al.

(10) Patent No.: US 10,995,053 B1
(45) Date of Patent: May 4, 2021

(54) HYDROXYTYROSOL URSOLIC ACID ESTER WITH ANTIOXIDANT ACTIVITY AND METHODS OF PREPARING THE SAME

(71) Applicants: Han Li, Xi'an (CN); Nan Hui, Xi'an (CN); Bin Tian, Xi'an (CN); Xingke Ju, Xi'an (CN); Yuzhi Liu, Xi'an (CN); Dan Yang, Xi'an (CN); Jingwen Xu, Xi'an (CN); Liang Qi, Xi'an (CN); Qianqian Zhao, Xi'an (CN); Yongbo Wang, Xi'an (CN)

(72) Inventors: Han Li, Xi'an (CN); Nan Hui, Xi'an (CN); Bin Tian, Xi'an (CN); Xingke Ju, Xi'an (CN); Yuzhi Liu, Xi'an (CN); Dan Yang, Xi'an (CN); Jingwen Xu, Xi'an (CN); Liang Qi, Xi'an (CN); Qianqian Zhao, Xi'an (CN); Yongbo Wang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/826,045

(22) Filed: Mar. 20, 2020

(51) Int. Cl.
    *C07C 67/08* (2006.01)
    *B01J 20/291* (2006.01)
    *B01J 31/02* (2006.01)

(52) U.S. Cl.
    CPC .......... *C07C 67/08* (2013.01); *B01J 20/291* (2013.01); *B01J 31/0231* (2013.01); *C07C 2603/52* (2017.05)

(58) Field of Classification Search
    CPC .... C07J 63/008; C07C 67/08; C07C 2603/52; B01J 31/0231
    See application file for complete search history.

(56) References Cited

U.S. PATENT DOCUMENTS

2016/0143930 A1\* 5/2016 Quintela Fernandez .................... A61K 31/19
    514/53

\* cited by examiner

*Primary Examiner* — Ana Z Muresan

(57) ABSTRACT

A compound having the formula (I):

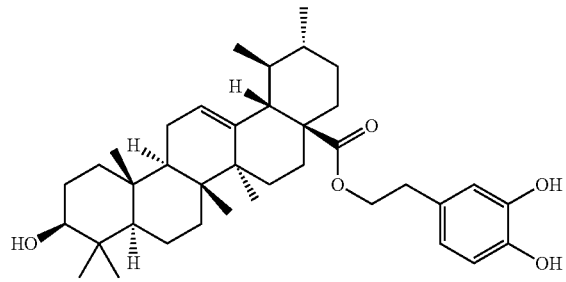

(I)

is disclosed. Methods of preparing the compound of formula (I) are also disclosed. The compound of formula (I) can be prepared by reacting a compound of formula (II) with a compound of formula (III) in an organic solvent with EDC (1-ethyl-3-(3-dimethylaminopropyl)carbodiimide). The compound of formula (I) can also be prepared by reacting the compound of formula (II) with the compound of formula (III) in 1-ethyl-3-methylimidazolium hexafluorophosphate as a solvent with silicomolybdic acid as a catalyst.

12 Claims, 3 Drawing Sheets

HYDROXYTYROSOL URSOLIC ACID ESTER WITH ANTIOXIDANT ACTIVITY AND METHODS OF PREPARING THE SAME

FIELD OF THE INVENTION

The present invention relates to food chemistry, more specifically, to a hydroxytyrosol ursolic acid ester, methods of preparing the same, and its antioxidant application.

BACKGROUND OF THE INVENTION

The oxidation of food will not only reduce the nutritional value of food, but also produce small molecular acids, ketones, aldehydes, etc., resulting in unpleasant odor. Food deterioration will bring great harm to human health and increase the incidence of inflammation and cancer. In order to improve the antioxidant capacity of food, processors often add some antioxidants in food processing. There is a need for new multi-functional antioxidants.

Hydroxytyrosol (compound of formula II) is a natural polyphenol, which has a variety of biological and pharmacological activities and can be derived from olive oil and wastewater from olive oil processing. Ursolic acid (compound of formula III) is a pentacyclic triterpenoid extracted from the evergreen trailing shrub of Azaleaceae.

In the present invention, the ursolic acid is combined with hydroxytyrosol to obtain a novel hydroxytyrosol ursolic acid ester, which has excellent antioxidant activity and high medical research and application value in the field of antioxidant health products.

SUMMARY OF THE INVENTION

In one embodiment, the present invention provides a compound having the following formula (I):

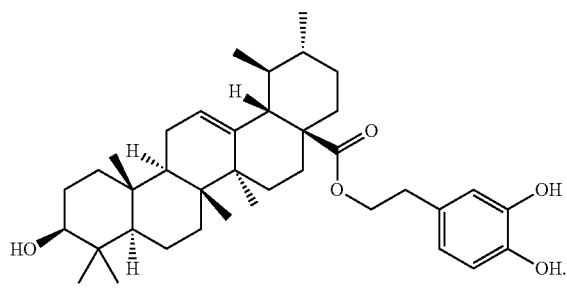

In another embodiment, the present invention discloses a method of preparing the compound of formula (I). The method includes reacting a compound of formula (II) with a compound of formula (III) in an organic solvent with EDC (1-ethyl-3-(3-dimethylaminopropyl)carbodiimide) as a catalyst to obtain the compound of formula (I):

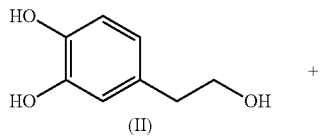

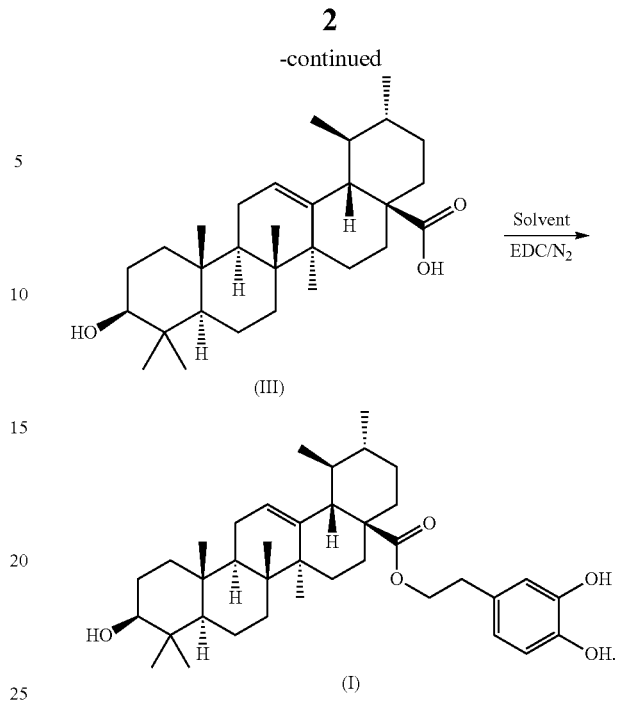

In another embodiment, the reaction of the compound of formula (II) with the compound of formula (III) includes the following steps: placing the compound of formula (II) and the compound of formula (III), in a molar ratio of 1:1 to 1:1.3, in a reactor; adding the organic solvent and EDC to obtain a reaction mixture; heating the reaction mixture at 50-80° C. for 4-8 hours; concentrating the reaction mixture under reduced pressure to give a crude product; and purifying the crude product on a silica gel column, eluting with petroleum ether/ethyl acetate solvent as an eluent, to obtain the compound of formula (I).

In another embodiment, the organic solvent is toluene, tetrahydrofuran or acetonitrile.

In another embodiment, the organic solvent is acetonitrile.

In another embodiment, the molar ratio of the compound of formula (II) and the compound of formula (III) is 1:1.1.

In another embodiment, the reaction mixture is heated at 70° C.

In another embodiment, the reaction mixture is heated for 6 hours.

In another embodiment, the eluent is petroleum ether:ethyl acetate=3:10.

In another embodiment, the present invention provide another method of preparing the compound of formula (I). The method includes reacting the compound of formula (II) with the compound of formula (III) in 1-ethyl-3-methylimidazolium hexafluorophosphate as a solvent with silicomolybdic acid as a catalyst to obtain the compound of formula (I):

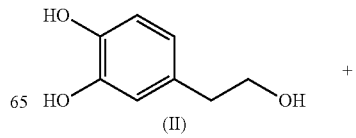

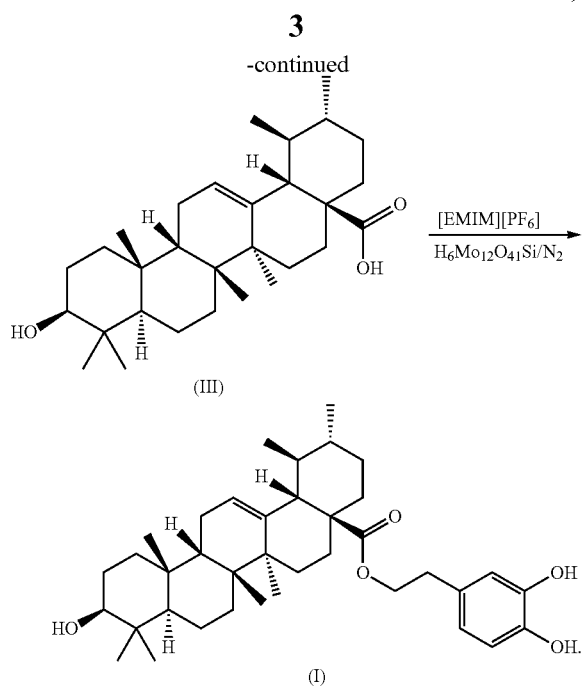

(III)

(I)

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding 1-ethyl-3-methylimidazolium hexafluorophosphate and silicomolybdic acid to obtain a reaction mixture; heating the reaction mixture at 25-50° C. for 5-10 hours; allowing the reaction mixture system to separate into layers; obtaining a crude product from one of the layers; and recrystallizing the crude product in method to obtain the compound of formula (I).

In another embodiment, 1-ethyl-3-methylimidazolium hexafluorophosphate is recycled and reused.

In another embodiment, the molar ratio of the compound of formula (II) and the compound of formula (III) is 1:1.1.

In another embodiment, the reaction mixture is heated at 25° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of Compound (1S,2R,4aS,6aS,6bR,8aR,10S, 12aR,12bR,14bS)-3,4-dihydroxyphenethyl 10-hydroxy-1,2, 6a,6b,9,9,12a-heptamethyl-1,2,3,4,4a,5,6,6a,6b,7,8,8a,9,10, 11,12,12a,12b,13,14b-icosahydropicene-4a-carboxylate (hydroxytyrosol ursolic acid ester, the Compound of Formula (I))

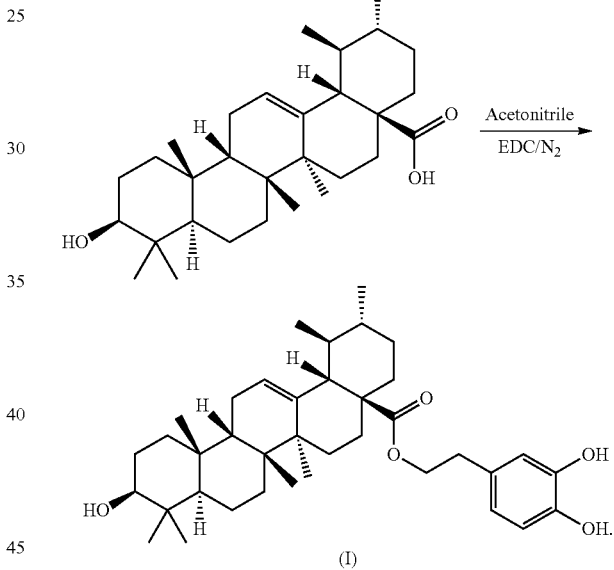

(I)

In a 100 mL three-necked flask, 49.3 mg (0.32 mmol) of hydroxytyrosol and 61.3 mg (0.32 mmol) EDC were dissolved in 30 mL of acetonitrile under nitrogen atmosphere. 159.7 mg (0.35 mmol) of ursolic acid was dissolved in 50 mL of acetonitrile, and added dropwise to the reaction mixture by a separatory funnel. After the completion of the dropwise addition, the temperature was raised to 70° C., and the reaction was carried out for 6 hours. Thin layer chromatography was used to track the reaction to completion. Heating was stopped, and the protective device was removed. The concentrated solution was washed with water, extracted with ethyl acetate, dried and concentrated, and a crude product was obtained. The crude product was purified by silica gel column chromatography, petroleum ether:ethyl acetate=3:10 as eluent, and the eluent was concentrated under reduced pressure and dried to obtain 154.9 mg of the titled compound, a yield of 81.71%.

$^1$H-NMR (400 MHz, DMSO-d$_6$) δ (ppm): 8.32 (1H, s), 7.92 (2H, s), 5.13 (3H, s), 4.22 (2H, t), 3.45 (1H, d), 3.12 (1H, t), 3.00 (2H, t), 2.50 (1H, t), 2.16-1.76 (4H, t), 1.52-

Figure 2:
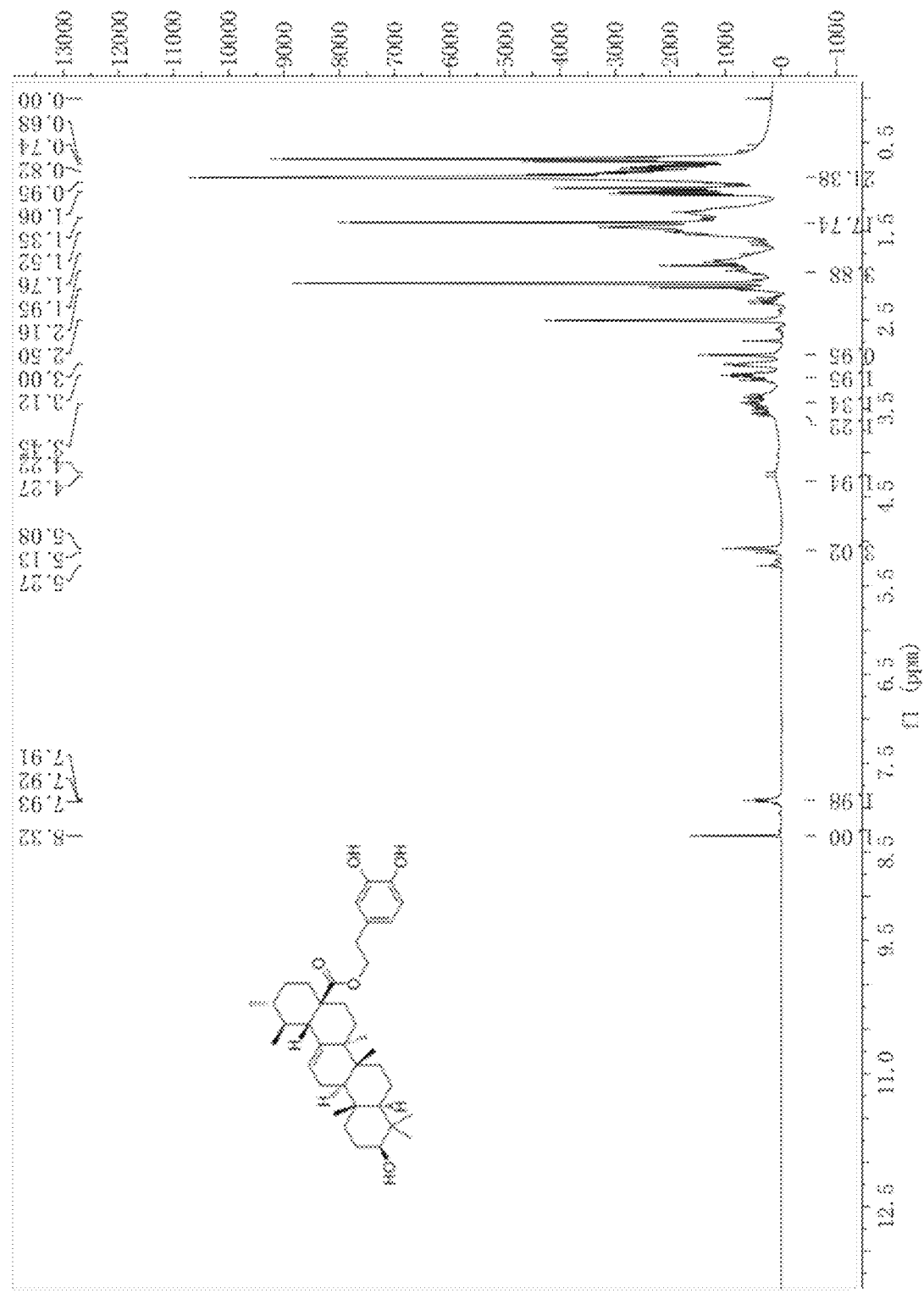
FIG. 2 is the $^1$H-NMR spectrum of the hydroxytyrosol ursolic acid ester (compound of formula (I)).
Figure 3:
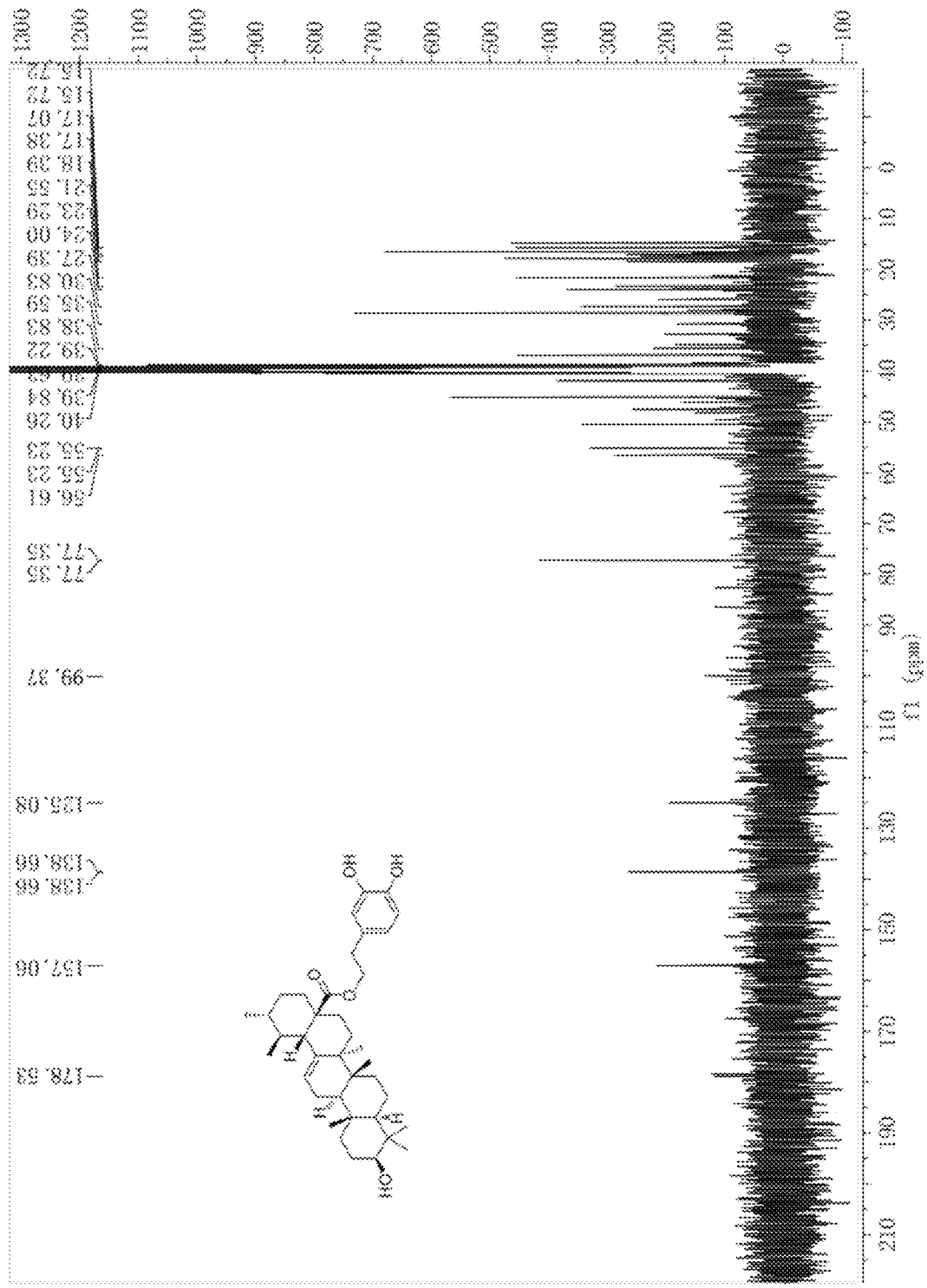
FIG. 3 is the $^{13}$C-NMR spectrum of the hydroxytyrosol ursolic acid ester (compound of formula (I)).

1.06 (18H, t), 0.95-0.68 (21H, s), shown in FIG. 2; $^{13}$C-NMR (400 MHz, DMSO-d$_6$) δ (ppm): 178.5, 157.0, 138.6, 125.0, 99.4, 77.3, 56.6, 55.2, 50.5, 47.5, 45.1, 41.9, 39.2, 38.8, 35.5, 30.8, 27.4, 24.0, 23.2, 21.6, 18.3, 17.3, 16.2, shown in FIG. 3.

Example 2

Preparation of the Compound of Formula (I)

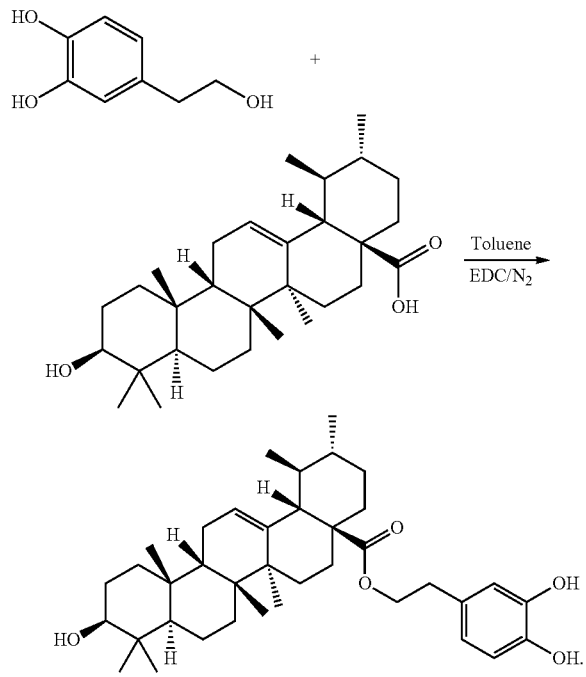

In a 100 mL three-necked flask, 49.3 mg (0.32 mmol) of hydroxytyrosol and 61.3 mg (0.32 mmol) EDC were dissolved in 30 mL of toluene under nitrogen atmosphere. 159.7 mg (0.35 mmol) of ursolic acid was dissolved in 50 mL of toluene, and added dropwise to the reaction mixture by a separatory funnel. After the completion of the dropwise addition, the temperature was raised to 50° C., and the reaction was carried out for 8 hours. Thin layer chromatography was used to track the reaction to completion. Heating was stopped, and the protective device was removed. The concentrated solution was washed with water, extracted with ethyl acetate, dried and concentrated, and a crude product was obtained. The crude product was purified by silica gel column chromatography, petroleum ether:ethyl acetate=3:10 as eluent, and the eluent was concentrated under reduced pressure and dried to obtain 150.0 mg of the titled compound, a yield of 79.14%.

Example 3

Preparation of the Compound of Formula (I)

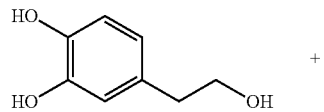

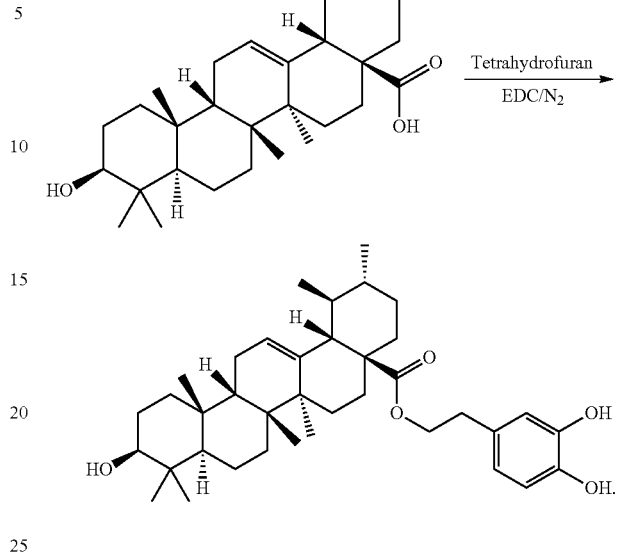

In a 100 mL three-necked flask, 49.3 mg (0.32 mmol) of hydroxytyrosol and 61.3 mg (0.32 mmol) EDC were dissolved in 30 mL of tetrahydrofuran under nitrogen atmosphere. 173.4 mg (0.38 mmol) of ursolic acid was dissolved in 50 mL of tetrahydrofuran, and added dropwise to the reaction mixture by a separatory funnel. After the completion of the dropwise addition, the temperature was raised to 80° C., and the reaction was carried out for 4 hours. Thin layer chromatography was used to track the reaction to completion. Heating was stopped, and the protective device was removed. The concentrated solution was washed with water, extracted with ethyl acetate, dried and concentrated, and a crude product was obtained. The crude product was purified by silica gel column chromatography, petroleum ether:ethyl acetate=3:10 as eluent, and the eluent was concentrated under reduced pressure and dried to obtain 135.5 mg of the titled compound, a yield of 71.47%.

Example 4

Preparation of the Compound of Formula (I)

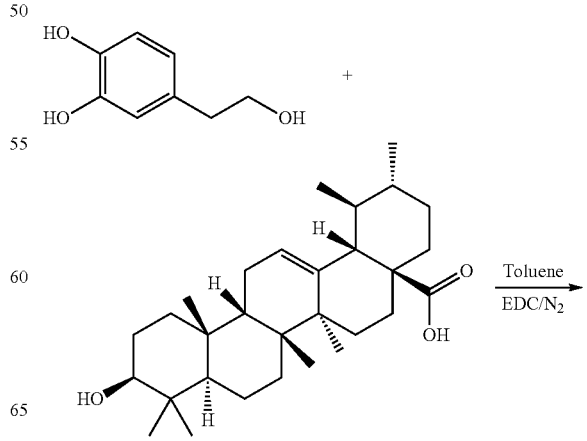

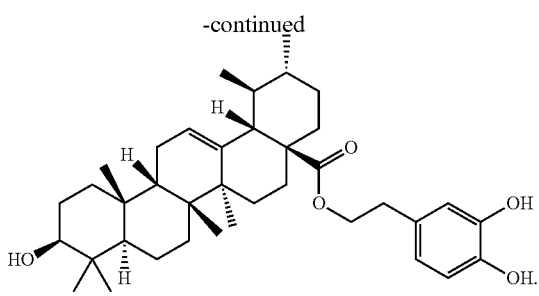

In a 100 mL three-necked flask, 49.3 mg (0.32 mmol) of hydroxytyrosol and 61.3 mg (0.32 mmol) EDC were dissolved in 30 mL of toluene under nitrogen atmosphere. 159.7 mg (0.35 mmol) of ursolic acid was dissolved in 50 mL of toluene, and added dropwise to the reaction mixture by a separatory funnel. After the completion of the dropwise addition, the temperature was raised to 75° C., and the reaction was carried out for 4 hours. Thin layer chromatography was used to track the reaction to completion. Heating was stopped, and the protective device was removed. The concentrated solution was washed with water, extracted with ethyl acetate, dried and concentrated, and a crude product was obtained. The crude product was purified by silica gel column chromatography, petroleum ether:ethyl acetate=3:10 as eluent, and the eluent was concentrated under reduced pressure and dried to obtain 132.6 mg of the titled compound, a yield of 69.95%.

Example 5

Preparation of the Compound of Formula (I)

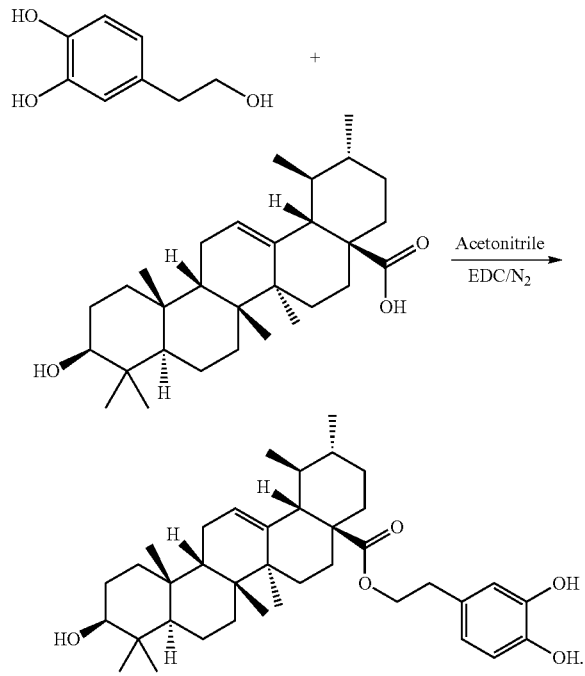

In a 100 mL three-necked flask, 49.3 mg (0.32 mmol) of hydroxytyrosol and 61.3 mg (0.32 mmol) EDC were dissolved in 30 mL of acetonitrile under nitrogen atmosphere. 146.0 mg (0.32 mmol) of ursolic acid was dissolved in 50 mL of acetonitrile, and added dropwise to the reaction mixture by a separatory funnel. After the completion of the dropwise addition, the temperature was raised to 70° C., and the reaction was carried out for 6 hours. Thin layer chromatography was used to track the reaction to completion. Heating was stopped, and the protective device was removed. The concentrated solution was washed with water, extracted with ethyl acetate, dried and concentrated, and a crude product was obtained. The crude product was purified by silica gel column chromatography, petroleum ether:ethyl acetate=1:6 as eluent, and the eluent was concentrated under reduced pressure and dried to obtain 146.8 mg of the titled compound, a yield of 77.46%.

Example 6

Preparation of the Compound of Formula (I)

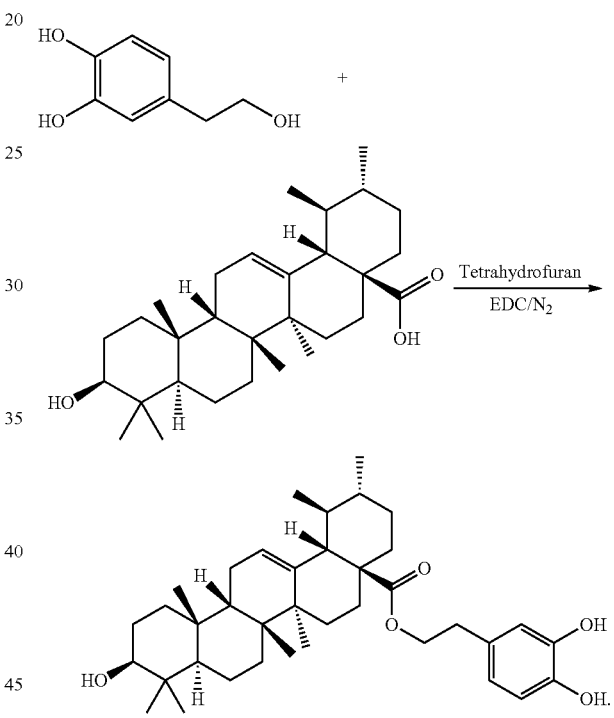

In a 100 mL three-necked flask, 49.3 mg (0.32 mmol) of hydroxytyrosol and 61.3 mg (0.32 mmol) EDC were dissolved in 30 mL of tetrahydrofuran under nitrogen atmosphere. 173.4 mg (0.38 mmol) of ursolic acid was dissolved in 50 mL of tetrahydrofuran, and added dropwise to the reaction mixture by a separatory funnel. After the completion of the dropwise addition, the temperature was raised to 60° C., and the reaction was carried out for 7 hours. Thin layer chromatography was used to track the reaction to completion. Heating was stopped, and the protective device was removed. The concentrated solution was washed with water, extracted with ethyl acetate, dried and concentrated, and a crude product was obtained. The crude product was purified by silica gel column chromatography, petroleum ether:ethyl acetate=1:6 as eluent, and the eluent was concentrated under reduced pressure and dried to obtain 116.0 mg of the titled compound, a yield of 61.18%.

Example 7

Preparation of the Compound of Formula (I)

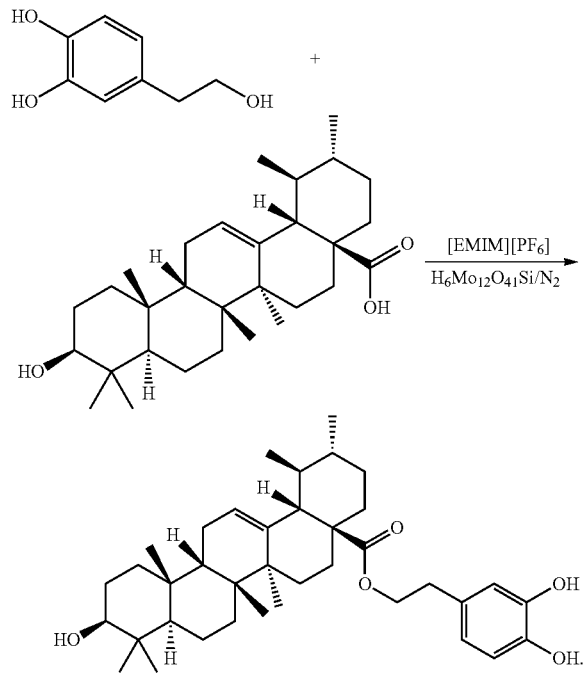

In a 100 mL three-necked flask, 49.3 mg (0.32 mmol) of hydroxytyrosol, 159.7 mg (0.35 mmol) of ursolic acid, and 5.5 mg (0.003 mmol) silicomolybdic acid were dissolved in 50 mL of 1-ethyl-3-methylimidazolium hexafluorophosphate (ionic liquid) under nitrogen atmosphere. After full dissolution, the temperature was raised to 25° C. and the reaction was carried out for 8 hours. Thin layer chromatography was used to track the reaction to completion, heating was stopped, and the protective device was removed. The reaction mixture system was allowed to separate into layers to give a crude product. The crude product was recrystallized with 50 mL methanol and dried to obtain 165.6 mg of the title compound, and the total yield was 87.35%.

Example 8

Preparation of the Compound of Formula (I)

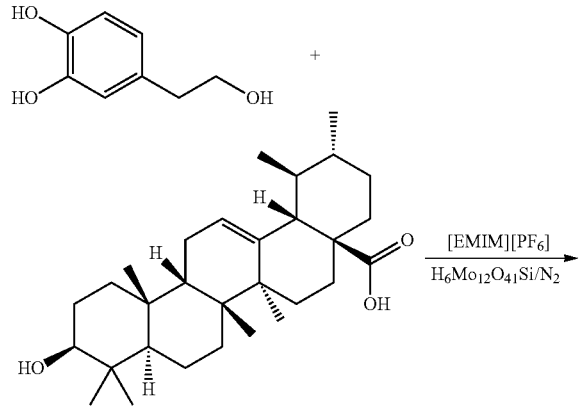

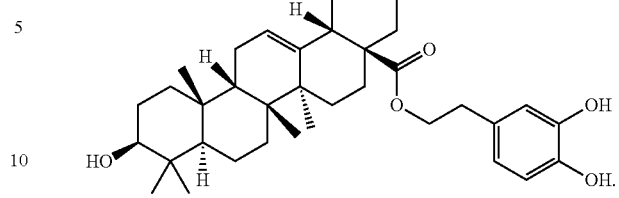

In a 100 mL three-necked flask, 49.3 mg (0.32 mmol) of hydroxytyrosol, 159.7 mg (0.35 mmol) of ursolic acid, and 5.5 mg (0.003 mmol) silicomolybdic acid were dissolved in 50 mL of 1-ethyl-3-methylimidazolium hexafluorophosphate under nitrogen atmosphere. After full dissolution, the temperature was raised to 50° C. and the reaction was carried out for 4 hours. Thin layer chromatography was used to track the reaction to completion, heating was stopped, and the protective device was removed. The reaction mixture system was allowed to separate into layers to give a crude product. The crude product was recrystallized with 50 mL methanol and dried to obtain 156.7 mg of the title compound, and the total yield was 83.12%.

Example 9

The antioxidant activity of the compound of formula (I) measured by a DPPH radical scavenging activity assay 2,2-Diphenyl-1-picryl hydrazyl (DPPH) is an organic compound composed of a stable organic radical. In the DPPH molecule, due to the presence of multiple electron-withdrawing —$NO_2$ and large $\pi$ bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in toluene to prepare a 0.2 mmoL/L DPPH solution, stored at 0° C. in dark.

Preparation of test solution: Vc (positive control), the compound of formula (I) (sample), hydroxytyrosol (control), and ursolic acid (control). The sample solution was subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 1).

TABLE 1

| Dilution gradient of the test solution | | |
|---|---|---|
| Number | Test solution | Concentration gradient/ppm |
| Vc | Vc | 1.76, 8.80, 21.12, 42.24, 79.20, 112.64, 281.60, 492.80, 792.00, 915.20 |
| A | Hydroxytyrosol ursolic acid ester | 1.76, 8.80, 21.12, 42.24, 79.20, 112.64, 281.60, 492.80, 792.00, 915.20 |

TABLE 1-continued

Dilution gradient of the test solution

| Number | Test solution | Concentration gradient/ppm |
|---|---|---|
| B | Hydroxytyrosol | 1.76, 8.80, 21.12, 42.24, 79.20, 112.64, 281.60, 492.80, 792.00, 915.20 |
| C | Ursolic acid | 1.76, 8.80, 21.12, 42.24, 79.20, 112.64, 281.60, 492.80, 792.00, 915.20 |

Specific Steps:

Sample liquid absorbance measurement: Take 2 mL of sample solution (Table 1 Vc, B, C), add 2 mL of DPPH solution with concentration of $2\times10^{-4}$ mol/L, mix and react in the dark at room temperature for 30 min, adjust to zero with toluene, and measure at 517 nm. The absorbance Ai was simultaneously measured for the absorbance Aj of 2 mL of toluene mixed with 2 mL of the sample solution and the absorbance Ao of 2 mL of DPPH solution mixed with 2 mL of toluene (The experimental results are shown in Table 2).

TABLE 2 absorbance test results of each test solution

| Sample | Absorbance | Concentration/ppm | | | | | | | | | |
|---|---|---|---|---|---|---|---|---|---|---|---|
| | | 1.76 | 8.80 | 21.12 | 42.24 | 79.20 | 112.64 | 281.60 | 492.80 | 792.00 | 915.20 |
| Vc | Ai | 0.718 | 0.624 | 0.222 | 0.142 | 0.091 | 0.078 | 0.076 | 0.070 | 0.074 | 0.065 |
| | Aj | 0.068 | 0.061 | 0.050 | 0.054 | 0.069 | 0.057 | 0.062 | 0.062 | 0.066 | 0.059 |
| | Ao | 0.846 | | | | | | | | | |
| A | Ai | 0.711 | 0.679 | 0.544 | 0.483 | 0.372 | 0.284 | 0.174 | 0.144 | 0.123 | 0.103 |
| | Aj | 0.051 | 0.049 | 0.058 | 0.062 | 0.054 | 0.047 | 0.057 | 0.043 | 0.059 | 0.055 |
| | Ao | 0.813 | | | | | | | | | |
| B | Ai | 0.918 | 0.904 | 0.810 | 0.739 | 0.630 | 0.580 | 0.403 | 0.365 | 0.268 | 0.254 |
| | Aj | 0.053 | 0.046 | 0.047 | 0.039 | 0.060 | 0.055 | 0.041 | 0.046 | 0.035 | 0.037 |
| | Ao | 0.935 | | | | | | | | | |
| C | Ai | 0.926 | 0.926 | 0.857 | 0.805 | 0.709 | 0.613 | 0.467 | 0.354 | 0.328 | 0.301 |
| | Aj | 0.047 | 0.052 | 0.044 | 0.053 | 0.061 | 0.047 | 0.037 | 0.042 | 0.045 | 0.039 |
| | Ao | 0.943 | | | | | | | | | |

Clearance calculation:clearance rate (%)=[1−(Ai−Aj)/Ao]*100%

TABLE 3

DPPH clearance rate experiment results

| Concentration/ppm | Clearance rate/% ( n = 3) | | | |
|---|---|---|---|---|
| | Vc | A | B | C |
| 1.76 | 23.16 | 18.75 | 7.42 | 6.77 |
| 8.80 | 33.47 | 22.56 | 8.16 | 7.25 |
| 21.12 | 79.63 | 40.18 | 18.43 | 13.82 |
| 42.24 | 89.55 | 48.23 | 25.10 | 20.22 |
| 79.20 | 97.42 | 60.88 | 38.99 | 31.24 |
| 112.64 | 97.53 | 70.75 | 43.87 | 39.89 |
| 281.60 | 98.29 | 85.63 | 61.25 | 54.31 |
| 492.80 | 99.06 | 87.52 | 65.88 | 66.82 |
| 792.00 | 99.10 | 92.13 | 75.03 | 69.94 |
| 915.20 | 99.28 | 94.11 | 76.76 | 72.25 |

Figure 1:
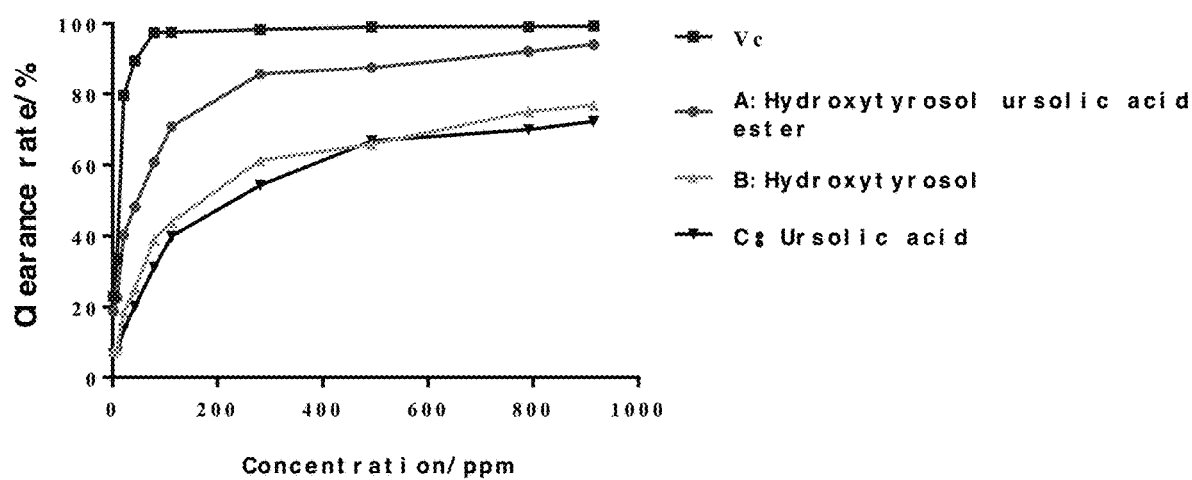
FIG. 1 shows the scavenging activity of the sample and control solutions at different concentrations.

As shown in FIG. 1 and Tables 1-3, the antioxidant activity of hydroxytyrosol ursolic acid ester (A) showed a concentration-dependent relationship, and the scavenging ability of compound A to DPPH radical increased with the increase of concentration. In the determined concentration range, the highest scavenging rate of DPPH radical was 94.11%. The scavenging ability of hydroxytyrosol ursolic acid ester (A) was similar to that of the positive control Vc group. Compared with the control group treated with hydroxytyrol (B) and ursolic acid (C) alone, the scavenging ability of hydroxytyrosol ursolic acid ester (A) to scavenge DPPH free radicals was much better at the same concentration. The above experimental results prove that the compound has excellent antioxidant activity and a good application prospect.

What is claimed is:

1. A compound having the following formula (I):

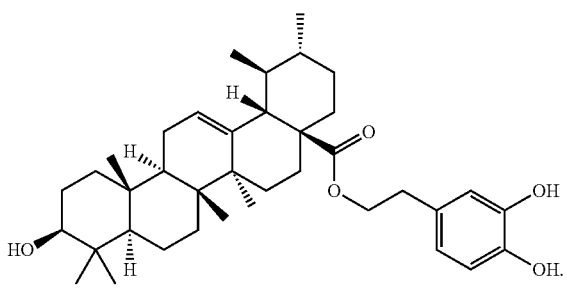

(I)

2. A method of preparing a compound of formula (I), comprising:

reacting a compound of formula (II) with a compound of formula (III) in an organic solvent with EDC (1-ethyl-3-(3-dimethylaminopropyl)carbodiimide) to obtain the compound of formula (I):

13

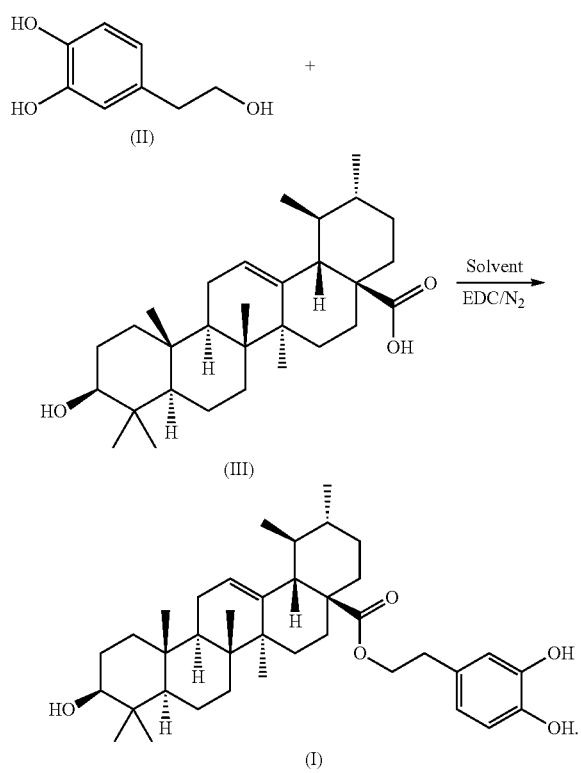

14 hexafluorophosphate as a solvent with silicomolybdic acid as a catalyst to obtain the compound of formula (I):

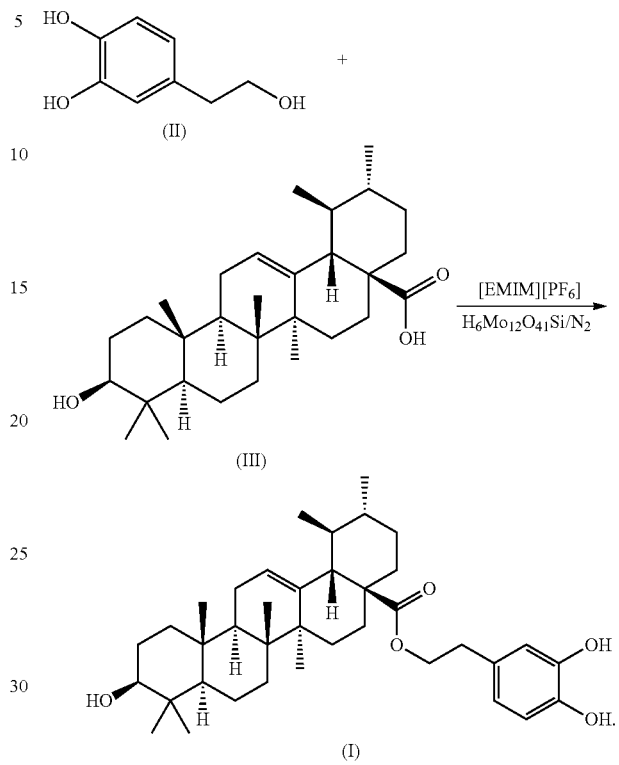

3. The method of claim 2, wherein the reaction of the compound of formula (II) with the compound of formula (III) comprises the following steps:
  placing the compound of formula (II) and the compound of formula (III), in a molar ratio of 1:1 to 1:1.3, in a reactor;
  adding the organic solvent and EDC to obtain a reaction mixture;
  heating the reaction mixture at 50-80° C. for 4-8 hours;
  concentrating the reaction mixture under reduced pressure to give a crude product; and
  purifying the crude product on a silica gel column, eluting with petroleum ether/ethyl acetate solvent as an eluent, to obtain the compound of formula (I).

4. The method of claim 3, wherein the organic solvent is toluene, tetrahydrofuran or acetonitrile.

5. The method of claim 3, wherein the reaction mixture is heated at 70° C.

6. The method of claim 3, wherein the reaction mixture is heated for 6 hours.

7. The method of claim 3, wherein the eluent is petroleum ether:ethyl acetate=3:10.

8. A method of preparing a compound of formula (I), comprising:
  reacting the compound of formula (II) with the compound of formula (III) in 1-ethyl-3-methylimidazolium 9. The method of claim 8, wherein the reaction of the compound of formula (II) with the compound of formula (III) comprises the following steps:
  placing the compound of formula (II) and the compound of formula (III), in a molar ratio of 1:1 to 1:1.3, in a reactor;
  adding 1-ethyl-3-methylimidazolium hexafluorophosphate and silicomolybdic acid to obtain a reaction mixture;
  heating the reaction mixture at 25-50° C. for 5-10 hours;
  allowing the reaction mixture system to separate into layers;
  obtaining a crude product from one of the layers; and
  recrystallizing the crude product in method to obtain the compound of formula (I).

10. The method of claim 9, wherein 1-ethyl-3-methylimidazolium hexafluorophosphate is recycled and reused.

11. The method of claim 9, wherein the reaction mixture is heated at 25° C.

12. The method of claim 9, wherein the reaction mixture is heated for 8 hours.

* * * * *